(12) United States Patent
Goudsmit et al.

(10) Patent No.: US 7,238,530 B2
(45) Date of Patent: Jul. 3, 2007

(54) ISOLATION AND AMPLIFICATION OF NUCLEIC ACID MATERIALS

(75) Inventors: Jaap Goudsmit, Amsterdam (NL); Cornelis Johannes Andreas Sol, Amsterdam (NL); Marcellinus Gualbertus Hubertus Maria Beld, Amstelveen (NL); Willem René Boom, Amsterdam (NL)

(73) Assignee: bioMerieux SA (FR)

( * ) Notice: Subject to any disclaimer, the term of this patent is extended or adjusted under 35 U.S.C. 154(b) by 0 days.

(21) Appl. No.: 09/760,085

(22) Filed: Jan. 12, 2001

(65) Prior Publication Data

US 2001/0021518 A1 Sep. 13, 2001

Related U.S. Application Data

(63) Continuation of application No. 09/125,241, filed as application No. PCT/NL97/00063 on Feb. 14, 1997, now abandoned.

(30) Foreign Application Priority Data

Feb. 14, 1996 (EP) .................................. 96200354

(51) Int. Cl.
- *C12Q 1/68* (2006.01)
- *C07H 21/02* (2006.01)
- *C07H 19/04* (2006.01)

(52) U.S. Cl. .................. 436/6; 435/91.2; 536/25.4; 536/25.41; 536/26.6

(58) Field of Classification Search .................... 435/6, 435/91.2; 536/25.4, 25.41, 26.6
See application file for complete search history.

(56) References Cited

U.S. PATENT DOCUMENTS

| | | | |
|---|---|---|---|
| 4,495,080 A | 1/1985 | Petit et al. | 252/179 |
| 4,965,188 A | 10/1990 | Mullis et al. | 435/6 |
| 5,043,272 A | 8/1991 | Hartley | 435/91 |
| 5,075,430 A | 12/1991 | Little | 536/27 |
| 5,155,018 A | 10/1992 | Gillespie et al. | 435/91 |
| 6,037,465 A | 3/2000 | Hillebrand et al. | 536/25.42 |
| 6,180,778 B1 * | 1/2001 | Bastian et al. | 536/25.4 |

FOREIGN PATENT DOCUMENTS

| | | |
|---|---|---|
| EP | 0 389 063 | 9/1990 |
| EP | 0 691 148 A2 | 1/1996 |
| WO | WO 95/21849 | 8/1975 |
| WO | WO 95/04140 | 2/1995 |
| WO | WO 95/06652 | 3/1995 |
| WO | 95/21849 * | 8/1995 |
| WO | WO 95/28409 | 10/1995 |
| WO | WO 95/34569 | 12/1995 |

OTHER PUBLICATIONS

Sambrook et al., Molecular Cloning, second edition p. 8.11-8.17.
Boom et al. "Rapid and Simple Method for Purification of Nucleic Acids" *Journal of Clinical Microbiology* 28(3):495-503 (1990).

* cited by examiner

*Primary Examiner*—Kenneth R. Horlick
*Assistant Examiner*—Joyce Tung
(74) *Attorney, Agent, or Firm*—Myers, Bigel, Sibley & Sajovec, P.A.

(57) ABSTRACT

The invention relates to methods for easily separating single stranded nucleic acid material from double stranded nucleic acid material in a sample containing both. By the right choice of at lease one chaotropic agent, preferably a guanidine salt, at a selected concentration and other suitable conditions such a chelating agents, pH and the like, it is possible to bind double stranded material to a solid phase such as silica particles, whereas single stranded material will not bind under those circumstances. By separating the silica particles from the sample the double stranded nucleic acid material is removed. It can easily be eluted from the silica particles. In a second step the single stranded material may be bound to a solid phase by selecting a different set of conditions. The particles can again be separated from the sample and the single stranded material may now be eluted. For very efficent separations, the process may be repeated. Following the separation of the two kinds of nucleic acid, either kind may be amplified. Methods of amplification are provided which do not need sequence data of the material to be amplified. In these methods a primer will be provided with an amplification motif and a random hybridization motif.

14 Claims, 8 Drawing Sheets

ISOLATION AND AMPLIFICATION OF NUCLEIC ACID MATERIALS

This application is a continuation of U.S. Ser. No. 09/125,241, filed Feb. 4, 1999, now abandoned which is the National Phase of PCT/NL97/00063, filed Feb. 14, 1997.

FIELD OF THE INVENTION

The invention relates to the field of purification and amplification of nucleic acids from nucleic acid containing starting materials, especially from biological materials such as urine, faeces, sperm, saliva, whole blood, serum or other body fluids, fractions of such fluids such as leucocyte fractions (buffy coats), cell cultures and the like, but also samples from the environment such as soil, water and the like.

BACKGROUND OF THE INVENTION

Until recently isolation and/or purification of nucleic acids from complex mixtures as described above was a laborious, multi-step procedure. In EP 0389063, incorporated herein by reference, a simple and rapid purification of nucleic acid material from a complex mixture is disclosed. This procedure comprises treating the complex mixture, such as whole blood with a chaotropic agent in the presence of a nucleic acid binding silica solid phase material under conditions that allow for binding of all nucleic acid material to said solid phase and separating said solid phase from the mixture. The reference shows that both single stranded and double stranded nucleic acids are bound to the solid phase if present in a mixture. The reference also discloses amplification (PCR) of a certain nucleic acid with a known sequence, suspected to be present in a mixture.

Thus, said reference teaches a simple and rapid detection method for known nucleic acids suspected to be present in a sample.

In many cases the nature of the target nucleic acid (double, stranded or single stranded) may not be known beforehand, or there may be many different targets necessary to be analyzed. In these cases the rapid but rather crude method described above may not be sophisticated enough and further separations of the crude material may be desired. Fractionation of mixtures of double-(ds) and single-stranded (ss) nucleic acids (NA) into single- and double-stranded forms is frequently needed e.g. in the separation of labelled ss-NA probes from ds-hybrids, in the separation of in vitro transcripts from ds-DNA templates, and in the separation of genomic DNA from mRNA. Currently, the separation of different kinds of nucleic acids can be accomplished by several techniques. Electrophoresis can be used to fractionate different forms of nucleic acids, because of differences in size and shape (1–3). Centrifugation takes advantage of differences in density (4), and more recently the technology of high-performance liquid chromatography (HPLC) has been applied to separate and purify single- and double-stranded DNA and RNA molecules (5–8).

RNA purified from eukaryotic cells by the currently most widely used procedure (9) appears to contain significant amounts of genomic DNA. An adaptation which reduces genomic DNA contamination of the ss-RNA fraction has recently been described (10).

It is not possible to look at single stranded and/or double stranded material separately using the method of EP 0389063 because the method does not discriminate between the two.

SUMMARY OF THE INVENTION

The present invention, therefore provides a method for separating single stranded nucleic acid material from double stranded nucleic acid material comprising contacting a mixture of the both with a liquid comprising a chaotropic agent and a nucleic acid binding solid phase, whereby the liquid has a composition such that double stranded nucleic acid binds to the solid phase and a substantial amount of single stranded nucleic acid does not and separating the solid phase from the liquid. Suitable circumstances to arrive at such a separation can be determined by the person skilled in the art.

BRIEF DESCRIPTION OF THE DRAWINGS

FIGS. 5A and 5B show the separation of ds-DNA and ss-RNA. NA was purified by protocol R-sup from a mixture of ds-DNA (1000 ng linearized pHC624, 2 kb) and ss-RNA (phage MS2 RNA, 800 ng). Final elution was in 50 µl TE and 25 µl or tenfold serial dilutions of the ss-NA fraction were electrophoresed through a 1% agarose gel (containing ethidium bromide) which was subsequently photographed under UV-illumination. FIG. 5A: upper row, lane 1, HindIII digested phage lambda DNA; lane 2, 100% recovery marker for ds-DNA and ss-RNA and serial tenfold dilutions thereof (lanes 3–6). Bottom row, output of protocol R-sup (lane 2) and tenfold serial dilutions (lanes 3–6). FIG. 5B: ds-DNA was subsequently transferred to a nitrocellulose filter and hybridized with a $^{32}$P-labelled probe homologous to input ds-DNA. ds-DNA and ss-RNA are indicated.

FIGS. 8A and 8B show how single-stranded nucleic acid was purified from samples containing HIV-1 RNA and TE (negative control) by protocol R-sup. and subsequently amplified with the non-selective RT-PCR. Panel A: lane 1, 100 bp DNA ladder; lanes 2 and 3 negative extraction controls; lanes 4 and 5 non-selectively amplified HIV-1 RNA; lanes 6, 7, 8 and 9 600, 60, 6 and 0 molecules resp. of pHCrec (positive PCR control). Panel B: Southern blot hybridization with $^{32}$P-labelled HIV-1 probes (containing the GAG, POL and ENV genes of HIV-1) of the samples shown in panel A. After overnight hybridization at 65° C. in 6×SSC, 0.1% SDS, 10% Dextran Sulphate and 50 μg/ml salmon sperm DNA, the filter was subsequently washed under high stringency conditions with 0.1 SSC/0.1% SDS at 65° C., and autoradiographed on X-ray film for two hrs. at −70° C. This experiment showed that most of the bands visible on the ethidium bromide stained agarose gel originated from the HIV-1 genome.

Circumstances under which double stranded material binds to the solid material and single stranded material will vary, however important parameters to obtain such differential binding are the concentration of the chaotropic agent, which should roughly be between 1–10 M, preferably between 3–6 M and particularly about 5 M; the concentration of chelating agent, which in the case of EDTA is applied should be equal to or greater than 10 mM and preferably not higher than 1 M; the pH of the aqueous solution in which the separation is carried out should be above 2 when a thiocyanate is used as chaotropic agent and it should be below 10 because otherwise there is a risk that the ds material will become ss. The temperature at which the process is carried out seems to be non-critical, however, it is probably best to keep it between 4° C. and 60° C. An important aspect of the process is of course that the ds material remains double stranded during the separation. Under the circumstances as disclosed above this will normally be the case if the ds nucleic acid is at least 50 bp long at 40% GC base pairs. The skilled artisan knows how this length may vary with lower or higher GC content. In Van Ness et al (26) and/or Thompson et al (27) it is shown that the whole process depends on intricate interactions between among others the factors mentioned above. Using this disclosure and the cited references the skilled artisan will be able to adjust the circumstances to his or her particular process.

Chaotropic agents are a very important feature of the present invention. They are defined as any substance that can alter the secondary, tertiary and/or quaternary structure of nucleic acids. They should have no substantial affect on the primary structure of the nucleic acid. If nucleic acids are present associated with other molecules, such as proteins, these associations can also be altered by the same or different chaotropic agents. Many chaotropic agents are suitable for use in the present invention, such as sodium iodide, potassium iodide, sodium (iso)thiocyanate, urea or guanidinium salts, or combinations thereof. A preferred class of chaotropic agents according to the invention are guanidinium salts, of which guanidinium thiocyanate is most preferred.

By serendipity we found that ss-nucleic acid did not bind to silica particles or diatomeous earth in the presence of buffer L11 (see examples), whereas ds nucleic acid did. Experiments with different circumstances showed that addition of $Mg^{2+}$ or other positive (bivalent) ions to the unbound fraction was of great importance. The best results were obtained with a concentration of bivalent ion ($Mg^{2+}$) about equal to the concentration of the chelating agent (EDTA).

The solid phase to be used is less critical. Important is that it should bind nucleic acids reversibly.

Many such materials are known, of which a number are silicium based, such as aluminium silicate and the like, preferably silica. Silica is meant to include $SiO_2$ crystals and other forms of silicon oxide, such as diatom skeletons, glass powder and/or particles and amorphous silicon oxide. The solid phase may be present in any form, it may even be the vessel which contains the nucleic acid mixtures or a part of such a vessel. It may also be a filter or any other suitable structure. Apart from silicium based materials other materials will also be suitable, such as nitrocellulose (filters), latex particles and other polymeric substances. A preferred form of the solid phase is a particulate form, which allows for easy separation of bound and free material, for instance by centrifugation. The particle size of the solid phase is not critical. Suitable average particle sizes range from about 0.05 to 500 μm. Preferably the range is chosen such that at least 80, preferably 90% of the particles have a size between the values just mentioned. The same holds true for the preferred ranges of which the average particle sizes are between 0.1 and 200 μm, preferably between 1 and 200 μm. The binding capacity of a given weight of the particles increases with decreasing size, however the lower limit of the size is that at which particles cannot easily be redispersed after separation through for instance centrifugation. This will be the case in starting material rich in nucleic acids containing many nucleic acids of a higher molecular weight. The particles and the nucleic acids may form aggregates in these cases. The person skilled in the art will be able to choose the right particle size for the particular application envisioned. The formation of aggregates may be avoided by using fractionated silica or diatomaceous earth in a number of applications.

A further embodiment of the present invention is a method for isolating single stranded nucleic acid material from a mixture of nucleic acid material, comprising the steps of subjecting the mixture to a method as described hereinabove and treating the supernatant containing the single stranded nucleic acid material with a second liquid comprising a chaotropic agent and a second nucleic acid binding solid phase, whereby the second liquid has a compositon such that the resulting mixture of supernatant and second liquid allow for binding of the single stranded nucleic acid material to the second solid phase.

This way the double stranded nucleic acid material is removed from the crude mixture and the single stranded nucleic acid is purified from the remaining still crude mixture in another single step. Both the double stranded material and the single stranded material are reversibly bound to the respective solid phases, so that they may be easily eluted from said solid phases to undergo further analysis or other treatments. A very useful further treatment is the amplification of the (double or single stranded) nucleic acid material.

Both types can be amplified, or both types may be converted into one another so that they can be amplified. The present invention provides in yet another embodiment a method for amplifying single stranded nucleic acid material comprising the steps of hybridizing the single stranded nucleic acid with primers and elongating the probes using an enzyme which adds nucleotides to the primer sequence using the hybridized single strand material as a template, whereby at least one primer comprises a random hybridizing sequence and an amplification motif.

Figure 7:
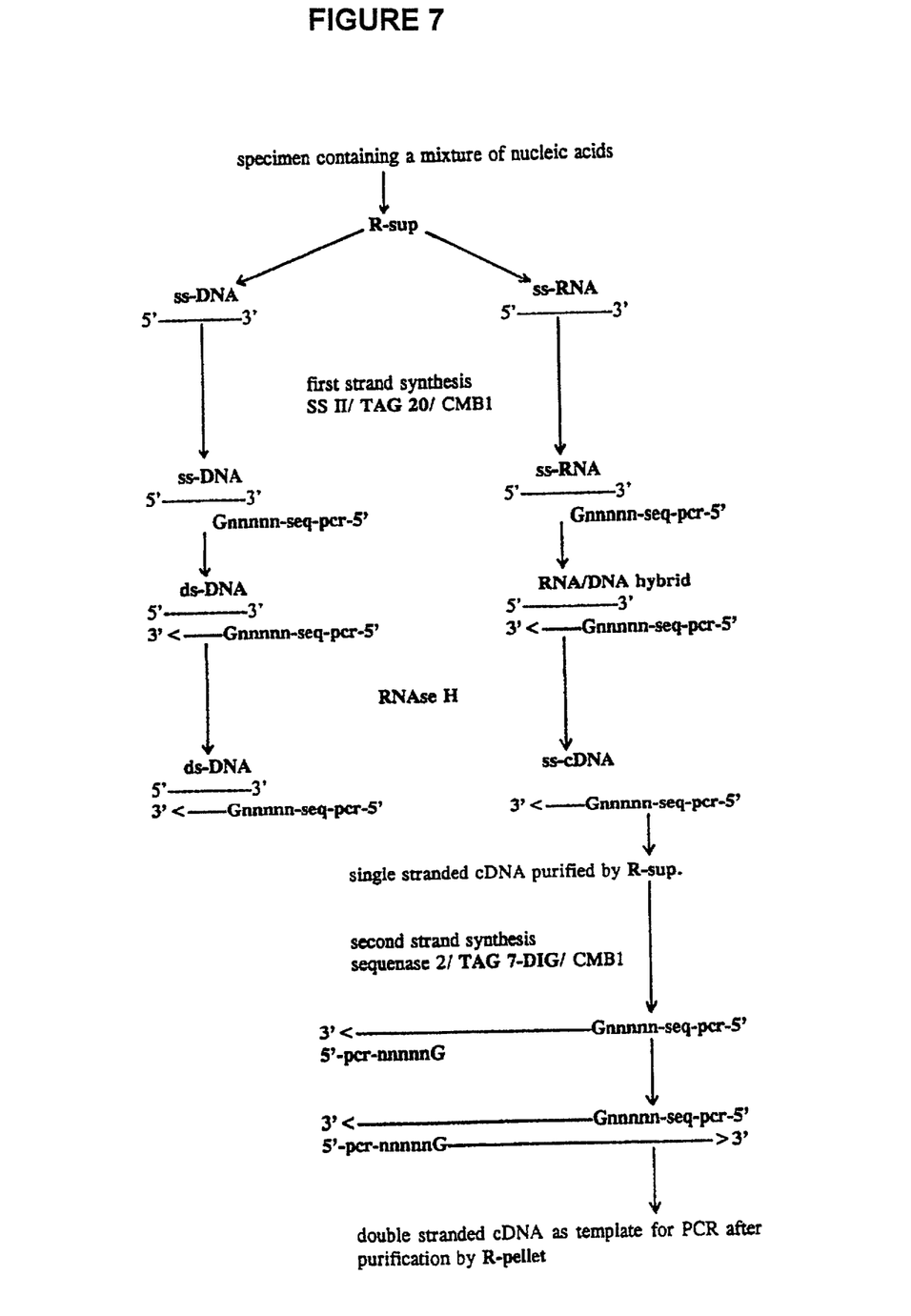
FIG. 7 is an outline of the procedure.

Single-stranded nucleic acids purified in accordance with the invention were used as input for a cDNA synthesis reaction using primers with random 3' ends (tagging primers) for the first and second strand synthesis (see the outline in FIG. 7).

These tagged cDNAs are then amplified by using only one PCR primer homologous to the PCR motif present in both tagging primers. The tagging primer used in the first strand synthesis (TAG 20) has been especially designed to facilitate subsequent direct sequencing of the resultant PCR products.

In contrast with most other protocols (16–22) the described method does not need any sequence data at all, and the majority of amplified products can be visualized on ethidium bromide stained agarose gels as discrete bands, which makes isolation and direct sequencing of the amplified cDNA feasible. The criteria for amplification are well known in the art. The length of suitable primers, suitable buffers, suitable melting temperatures for separating strands, and suitable hybridization conditions can all be determined using standard handbooks in the field.

Of course the sequences which are exemplified can be varied without departing from the present invention. It is not so much important what sequence is used as an amplification motif, as long as it is suitable for hybridization and primer extension purposes. Suitable limits depend on the conditions which can be varied by the person skilled in the art. Usually primers will be at least 10 bases long and not much longer than 100 bases.

The amplification embodiments of the invention are exemplified using PCR (polymerase chain reaction). Other amplification methods are of course equally suitable.

The exemplified label (or tag) on the primers is DIG (digoxygenin). However other labels are available and well known in the art.

The invention will now be explained in further detail in the following detailed description.

Separation/Isolation

Materials and Methods

Source of Nucleic Acids.

Phage MS-2 ss-RNA (3569 nt), *E. coli* rRNA (16 and 23S; 1,7 kb and 3,5 kb respectively), phage M13 ss-DNA (7599 nt) and HindIII digested phage lambda ds-DNA were purchased from Boehringer (Mannheim, Germany). Rotavirus ds-RNA was purified from feces of an infected individual by protocol Y/SC (11). Plasmid DNA was purified from *E. coli* HB101 as described by Ish-Horowicz and Burke (13) followed by column chromatography with Sepharose CL2B (Pharmacia, Inc. Uppsala, Sweden). Total NA was purified from *E. coli* by protocol Y/D (11).

Chemicals.

Guanidinium thiocyanate (GuSCN) was obtained from Fluka (Buchs, Switzerland).

EDTA (Titriplex) and $MgCl_2.6H_2O$ were obtained from Merck (Darmstadt, Germany). Tris was obtained from Boehringer (Mannheim, Germany). The preparation of size-fractionated silica particles (silica coarse, SC) and diatom suspension has been described (11). TRITON X-100™ (polyethoxylated p-isooctyl-phenol) was from Packard (Packard Instrument Co., Inc., Downers Grove, Ill.).

Composition of Buffers.

The lysis/binding buffer L6, washing buffer L2, and TE (10 mM Tris.HCl, 1 mM EDTA; pH=8.0) was made by dissolving 37.2 g EDTA (Merck, Germany) and 4.4 g NaOH (Merck, Germany) in aqua in a total volume of 500 ml. Lysis/binding buffer L11 was made by dissolving 120 g of GuSCN in 100 ml 0.2M EDTA (pH=8.0). Binding buffer L10 was prepared by dissolving 120 g GusCN in 100 ml 0.35M TRIS.HCl (pH 6.4); subsequently 22 ml 0.2M EDTA (pH 8.0) and 0.1 g TRITON X-100™ (polyethoxylated p-isooctyl-phenol) were added and the solution was homogenized; finally 11 g of solid $MgCl_2.6H_2O$ was added. The final concentration of $MgCl_2$ in L10 is about 0.25M. L10 is stable for at least 1 month when stored at ambient temperature in the dark.

Fractionation of ds-NA and ss-NA by Protocol R.

Figure 1:
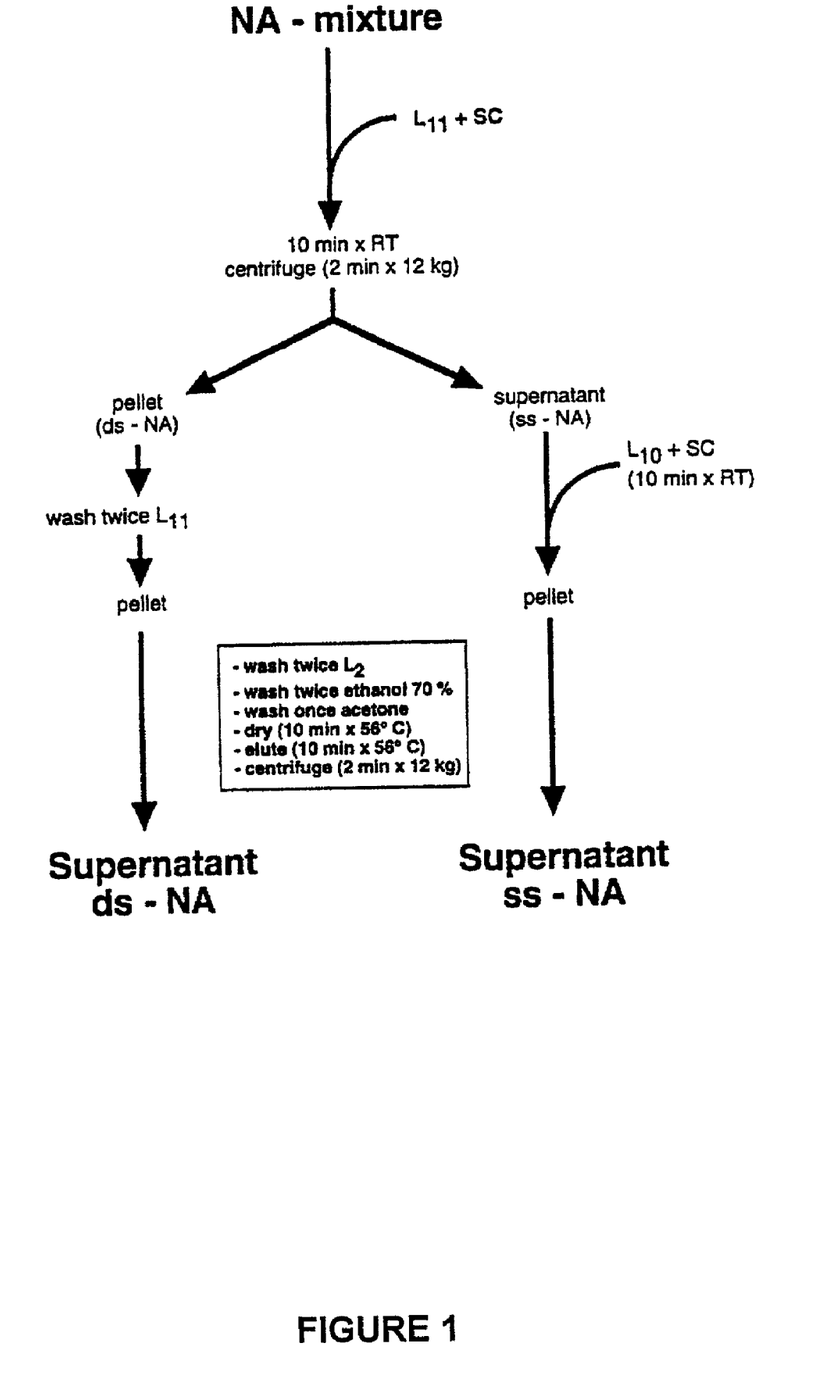
FIG 1 is an outline of protocol R. Recovery of ds-NA takes place from the initial pellet (R-pellet), recovery of ss-NA takes place from initial supernatant (R-sup) L11, L10, L6 and L2 are GuSCN-based buffers, SC is silica particle suspension.

The procedure is outlined in FIG. 1. A 50 μl specimen (containing a mixture of NA-types in TE buffer) was added to a mixture of 900 μl L11 and 40 μl SC in an Eppendorf tube and was subsequently homogenized by vortexing. After 10 min. binding at room temperature, the tube was centrifuged (2 min. at approx. 10.000×g) which resulted in a silica/ds-NA pellet ("initial silica pellet") and a supernatant containing ss-NA.

To recover ss-NA forms (protocol R-sup), 900 μl of the supernatant were added to a mixture of 400 μl L10 and 40 μl SC and ss-NA was bound during a 10 min. incubation at room temperature. The tube was subsequently centrifuged (15 sec. at approx. 10.000×g), and the supernatant was discarded (by suction). The resulting pellet was subsequently washed twice with 1 ml of L2, twice with 1 ml ethanol 70% (vol/vol) and once with 1 ml acetone. The silica pellet was dried (10 min. at 56° C. with open lid in an Eppendorf heating block) and eluted in 50 μl TE buffer (10 min. at 56° C.; closed lid). After centrifugation (2 min. at approx. 10.000×g) the supernatant contains the ss-NA fraction To recover ds-NA forms (protocol R-pellet) from the initial silica pellet, the remaining supernatant was discarded, and the silica pellet was washed twice with L11 to remove unbound ss-NA. The resulting silica pellet was subsequently washed twice with L2, twice with ethanol 70%, once with acetone, dried and eluted as described above. After centrifugation (2 min. at approx. 10.000×g) the supernatant contains the ds-NA fraction.

In the complete procedure (which takes about one hour) for fractionation of NA by protocol R, only two Eppendorf tubes are used.

Fractionation of Genomic DNA and ss-NA.

Due to trapping of ss-NA into high-molecular-weight genomic DNA, protocol R as described above gives only low yields of ss-NA. This can be circumvented by first isolating total NA by protocol Y/D (11), which causes some shearing of the high-molecular-weight genomic DNA, sufficient enough to prevent trapping of the ss-NA. Total NA thus purified can subsequently be used as input for protocol R.

Gel Electrophoresis.

In all experiments, NA was electrophoresed (8 to 10 V/cm) through neutral agarose slab gels containing ethidium bromide (1 µg/ml) in the buffer system (40 mM TRIS-20 mM sodium acetate-2 mM EDTA adjusted to pH 7.7 with acetic acid; ethidium bromide was added to a concentration of 1 µg/ml of buffer) described by Aaij and Borst (14).

Hybridization.

DNA fragments were transferred to nitrocellulose filters by the procedure of Southern (15) and hybridized with [alpha-$^{32}$P]dCTP labelled pHC624 (16) prepared by random labeling (Boehringer, Germany). Hybridization conditions were as described previously (12).

Results

Comparison of different GuSCN-containing lysis buffers with respect to the binding of different NA-types to silica particles revealed that only doublestranded forms were bound when using L11 (which is about 100 mM for EDTA) as binding buffer; on the other hand both double- and single-stranded forms were bound in binding buffer L6 (which is about 20 mM for EDTA) (Table 1). These observations formed the basis for the development of a protocol (Protocol R) for the fractionation of single-stranded nucleic acids and double-stranded nucleic acids (FIG. 1)

Once double-stranded nucleic acid is bound by silica particles in L11, a brief centrifugation will separate the silica/ds-NA pellet from the supernatant containing the single-stranded forms. Addition of this supernatant to a mixture of silica particles and binding buffer L10 (which is about 250 mM for Mg$^{2+}$) the binding of single-stranded nucleic acids to the silica particles is restored. Double-stranded and single-stranded forms can subsequently be purified by washing and eluting the silica-NA complexes (protocol R). Double-stranded nucleic acid is recovered from the initial silica pellet (protocol R-pellet), whereas single-stranded forms are recovered from the initial supernatant (protocol R-sup).

For optimization of protocol R we performed reconstruction experiments in which previously purified or commercially available, nucleic acids were mixed and subsequently fractionated by protocol R.

Fractionation of a Mixture of Double-stranded DNA and Single-stranded DNA.

Figure 2:
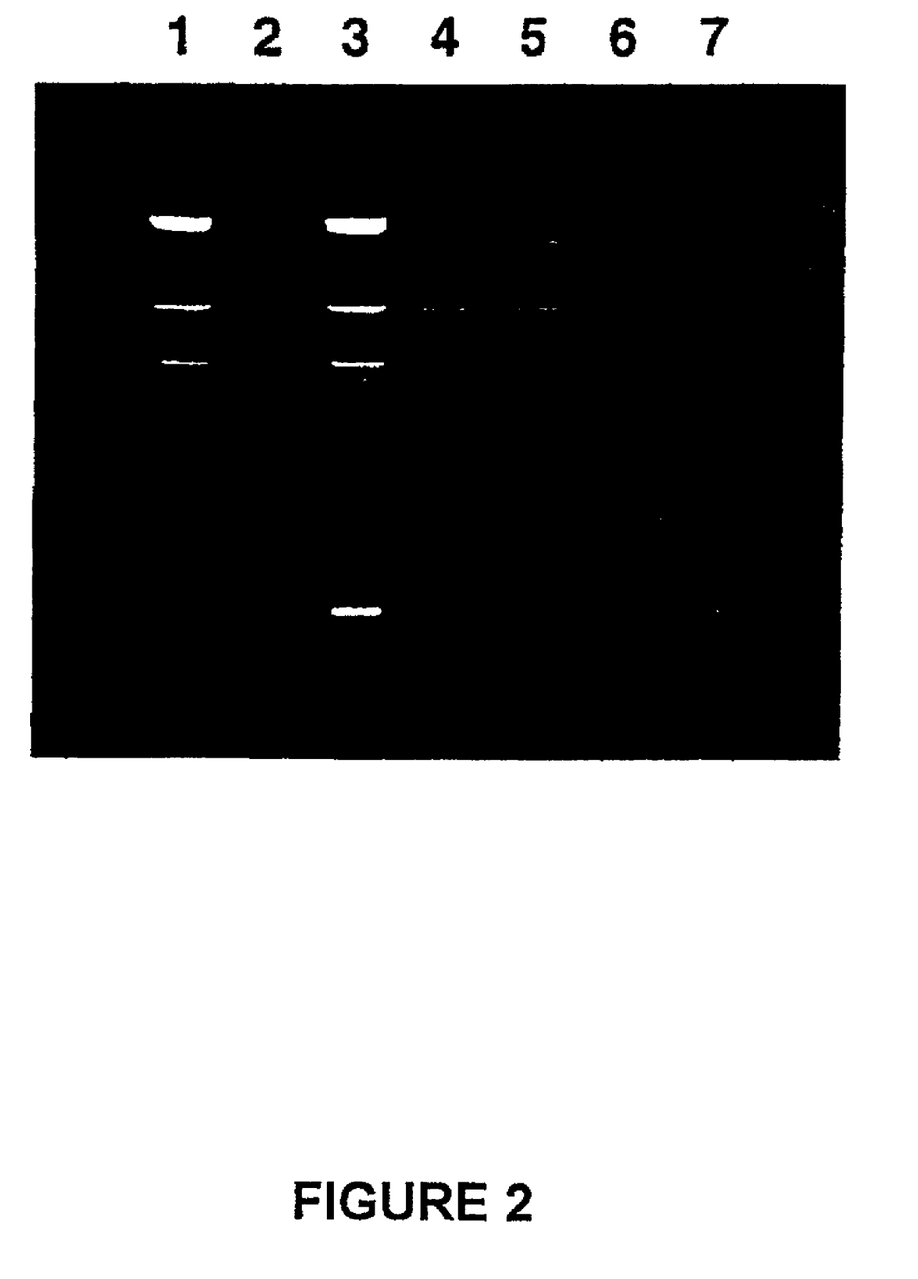
FIG. 2 shows the separation of ds-DNA and ss-DNA. NA was purified (in duplicate) by protocol R from a mixture of ds-DNA (phage lambda, HindIII digest, 1 µg) and ss-DNA (phage M13 DNA, 500 ng) Final elutions were in 50 µl TE and 25 µl were electrophoresed through a 1% agarose gel (containing ethidium bromide), which was subsequently photographed under UV-illumination. Lane 1, 100% recovery marker for ds-DNA fragments; lane 2, 100% recovery marker ss-DNA; lane 3, 100% recovery marker mixture ds-DNA/ss-DNA. Lanes 4 and 5, output protocol R-pellet; lanes 6 and 7, output protocol R-sup.

The fractionation of a ds-DNA/ss-DNA mixture, into double stranded- and single stranded forms is shown in FIG. 2. The recovery estimated from the band intensity of the ethidium bromide stained gel for ss-DNA was about 50%, the estimated recovery of ds-DNA in the range of 500 bp to 4,6 kb was 80%–90% [similar recoveries were obtained for ds-DNA fragments in the range of 100–500 bp (not shown)], larger fragments were significantly sheared as noted before (11). At the level of detection by UV-illumination, fractionation into ds- and ss-forms was complete.

Fractionation of a Mixture of Double-stranded RNA and Single-stranded RNA.

Figure 3:
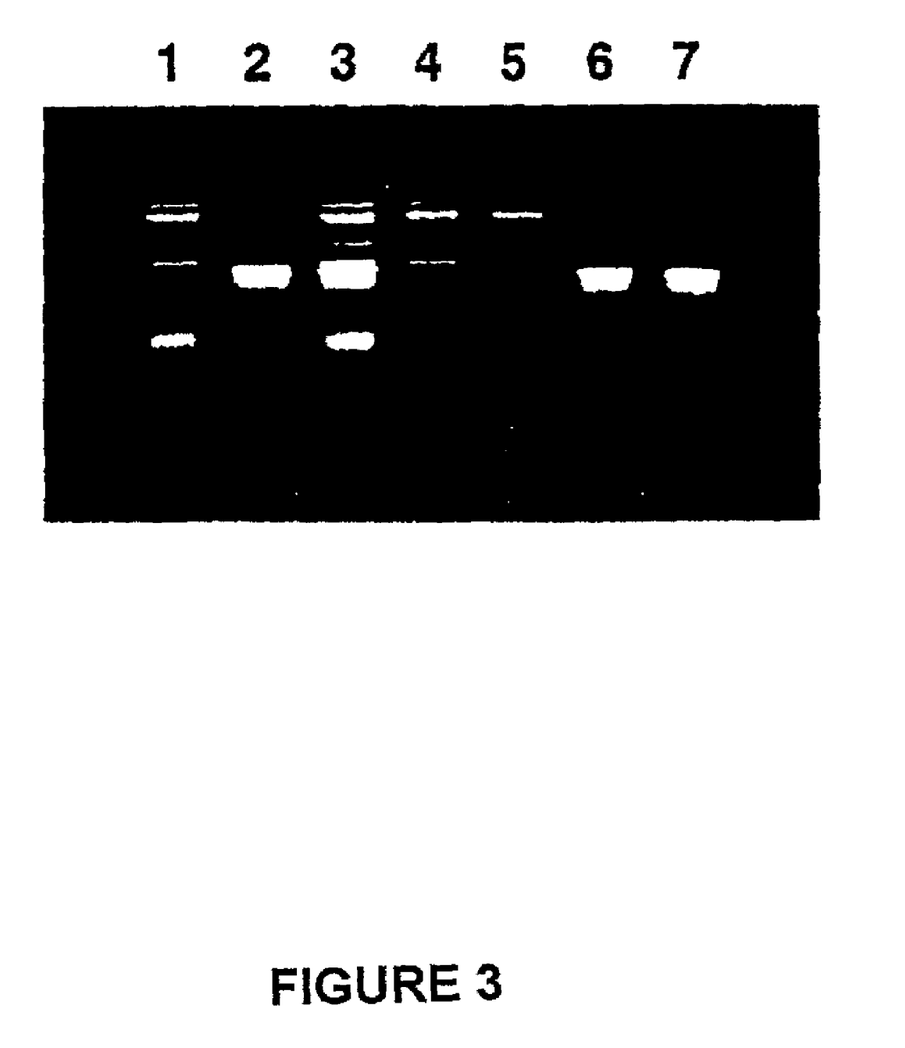
FIG. 3 shows the separation of ds-RNA and ss-RNA. NA was purified (in duplicate) by protocol R from a mixture of ds-RNA (Rotavirus ds-RNA) and ss-RNA (phage MS2 RNA, 800 ng). Final elutions were in 50 µl TE and 25 µl were electrophoresed through a 1% agarose gel (containing ethidium bromide) which was subsequently photographed under UV-illumination. Lane 1, 100% recovery marker for ds-RNA fragments; lane 2, 100% recovery marker ss-RNA; lane 3, 100% recovery marker ds-RNA/ss-RNA mixture. Lanes 4 and 5, output protocol R-pellet; lanes 6 and 7, output protocol R-sup.

FIG. 3 shows the fractionation of a mixture of ds-RNA (human Rotavirus genome segments 1–11; for review see 14) and ss-RNA (phage MS2 RNA) into double stranded- and single stranded forms. The estimated recovery of ds-RNA and ss-RNA was at least 80%. At the level of detection by UV-illumination, fractionation into ds- and ss-forms was complete.

Fractionation of a Mixture of Double-stranded DNA and Single-stranded RNA.

Figure 4:
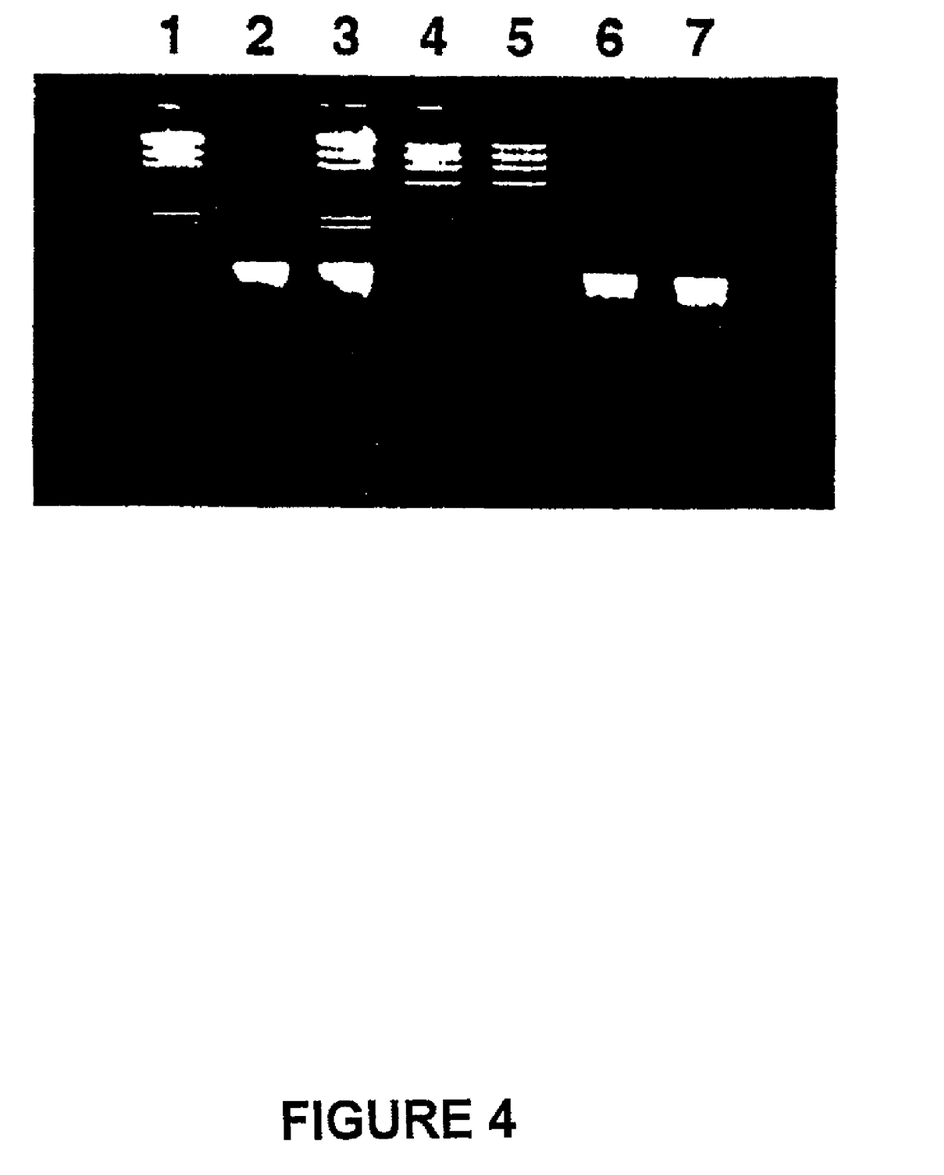
FIG. 4 shows the separation of ds-DNA and ss-RNA. NA was purified (in duplicate) by protocol R from a mixture of ds-DNA (750 ng phage lambda digested with hindIII) and ss-RNA (phage MS2 RNA, 800 ng). Final elutions were in 50 µl TE and 25 µl were electrophoresed through a 1% agarose gel (containing ethidium bromide) which was subsequently photographed under UV-illumination. Lane 1, 100% recovery marker for ds-DNA; lane 2, 100% recovery marker for ss-RNA; lane 3, 100% recovery marker for ds-DNA/ss-RNA mixture. Lanes 4 and 5, output protocol R-pellet; lanes 6 and 7, output protocol R-sup.

In FIG. 4 it is shown that ds-DNA can also efficiently be separated from ss-RNA.

Again are the recoveries for both fractions are at least 80%. Similar results were obtained when E. coli rRNA (23S and 16S) was used as ss-RNA input (not shown).

Figure 5:
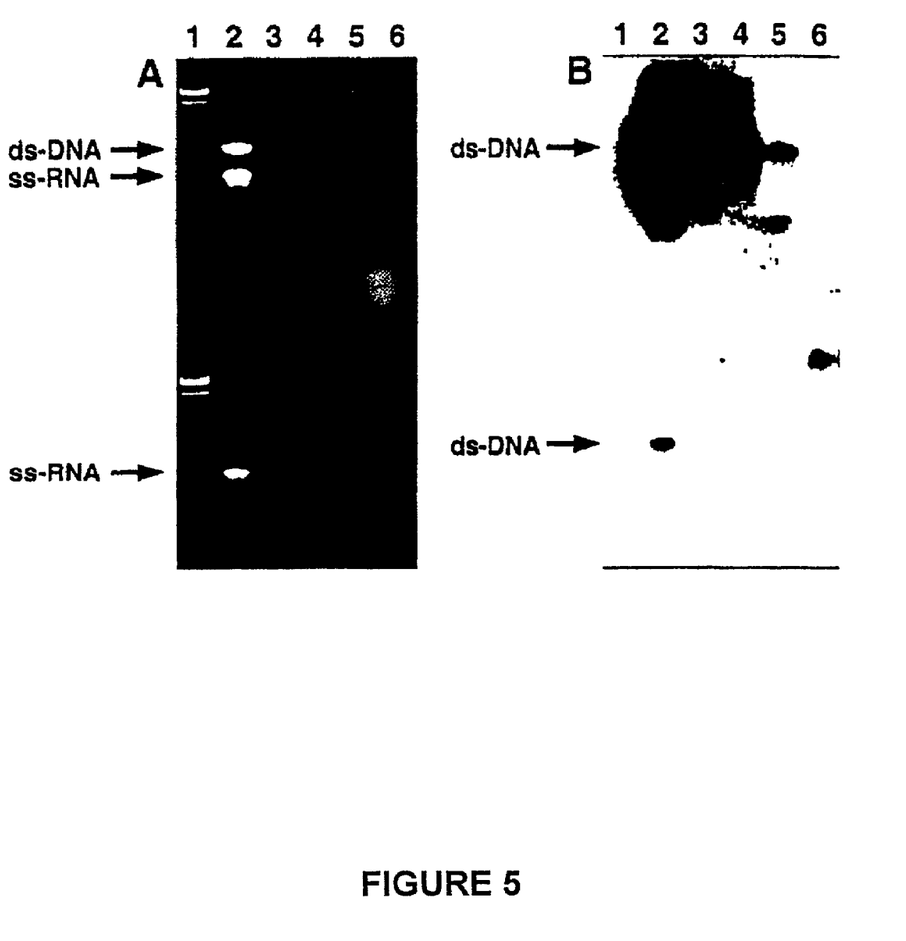

In the experiments described above, fractionation of ds- and ss-NA forms (as judged by visual inspection of band intensities after ethidium bromide staining and UV illumination) appeared to be complete. In order to establish the performance of the fractionation procedure for a mixture of ds-DNA and ss-RNA into ss- and ds-forms, NA purified by protocol R-sup from such a mixture was studied by Southern blotting and hybridization with a $^{32}$P-labelled DNA probe, homologous to the ds-DNA used as input for fractionation. This experiment revealed that the ss-NA fraction contained less than 0.1% of the ds-DNA input (FIG. 5).

Fractionation of a Mixture of Genomic DNA and Single-stranded RNA.

Figure 6:
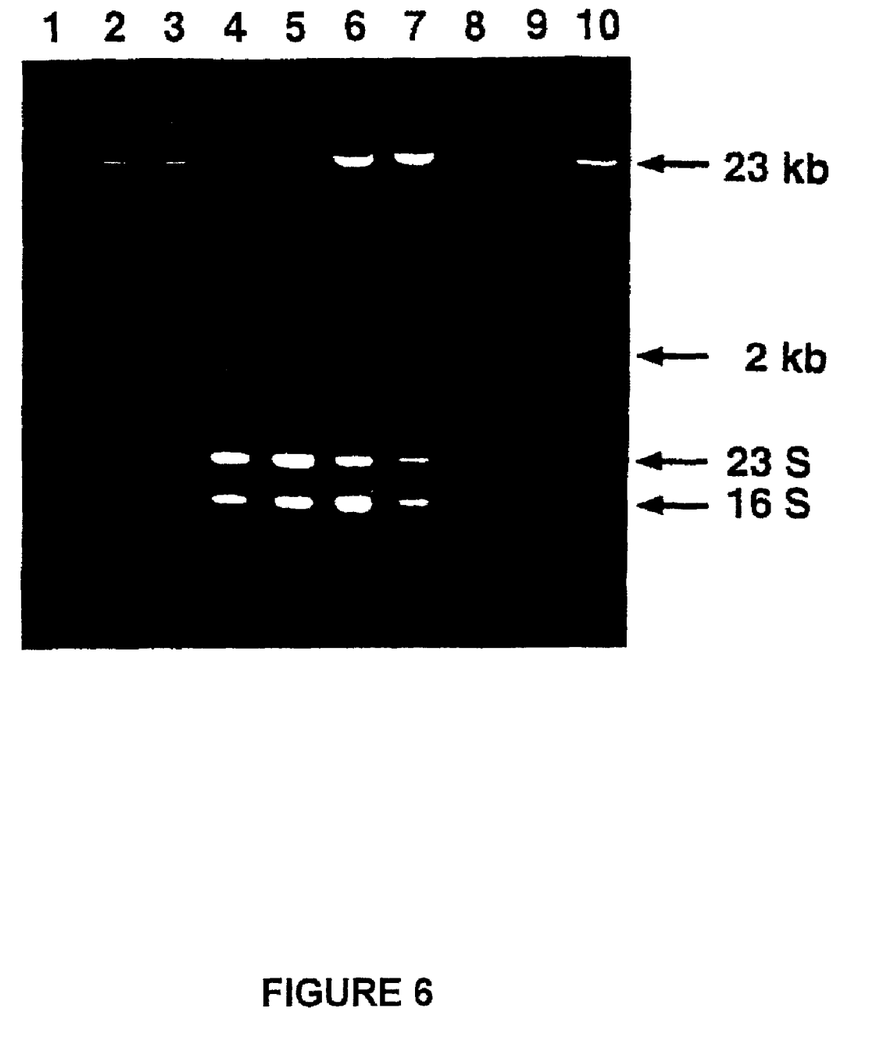
FIG. 6 shows the separation of genomic DNA from ss-RNA and how to deal with trapping of ss-RNA. *E. coil* were directly used as input material for duplicate extractions by protocol R (lanes 6 and 7, R-pellet: lanes 8 and 9). Alternatively, total NA was first purified by protocol Y using diatoms as NA-carrier (which causes shearing of genomic DNA). The purified nucleic acids were subsequently used as input for protocol R (lanes 2 and 3, R-pellet; lanes 4 and 5, R-sup). Final elutions were in 50 μl TE and 25 μl were electrophoresed through a 1% agarose gel (containing ethidium bromide) which was subsequently photographed under UV-illumination. Marker lanes 1 and 10 (500 ng phage lambda DNA, HindIII digested). 23S and 16S rRNA, and ds-DNA molecular weight markers (23 kb and 2.0 kb) are indicated.

When we investigated the separation of high-molecular-weight (genomic) dsDNA and ss-RNA by direct fractionation using E. coli as input for protocol R, it appeared that the ds-DNA fraction was heavily contaminated with rRNA (FIG. 6, lanes 6 and 7), and ss-RNA recovery was low (FIG. 6, lanes B and 9). This was likely due to trapping of RNA into high-molecular-weight (genomic) ds-DNA when silica/NA complexes were formed. On the other hand no genomic DNA was observed in the ss-RNA fraction. Total nucleic acid, which was first isolated using the standard protocol Y/D (11), and hereafter used as input material in protocol R showed significantly higher recoveries of the ss-RNA fraction (FIG. 6, lanes 2 and 5).

Amplifications

Materials and Methods

Source of Nucleic Acids.

HIV-1 RNA was isolated from a virus culture (23), phage MS-2 RNA was purchased from Boehringer (Mannheim, Germany) and the 7.5 Kb Poly(A)Tailed RNA and the 100 bp ladder used as a marker were purchased from Life Technologies (Gaithersburg, Md., USA). The PCR TA3 cloning vector was obtained from Promega (Madison, USA). Plasmids 5' NOT Hxb$_2$ENN (24) {containing the GAG and POL genes of HIV-1 from nucleotide 638–4647} and 168.1 RTN (24) {containing the ENV gene of HIV-1 from nucleotide 5674–8474} were purified as described by Ish-Horowicz and Burke (13) followed by protocol R-pellet as described in the examples. The plasmid pHCrec used as a positive control in the PCR experiments was made by a low annealing PCR on lambda DNA (Boehringer) using PCR primer RB 8 (see below). The discrete PCR products were purified using protocol Y/D (11) and subsequently cloned in a PCR III vector (Invitrogen). The revealing plasmid, pHCrec with a approximately 600 bp insert was subsequently purified from E. coli HB101 as described by Ish-Horowicz and Burke (13) followed by column chromatography with Sepharose CL2B (Pharmacia, Inc. Uppsala, Sweden).

Chemicals and Enzymes

EDTA, KCl, MgCl$_2$.6H$_2$O, NaCl and tri-Sodium citrate dihydrate were obtained from Merck (Darmstadt, Germany). TRIS and BSA were obtained from Boehninger (Mannheim, Germany). TRITON X-100™ (polyethoxylated p-isooctyl-phenol) was obtained from Packard (Packard Instruments Co., Inc., Downers, Ill., USA). Sodium Dodecylsulfate (SDS) was obtained from Serva (Heidelberg, Germany).

The dNTP's and Dextran Sulphate were obtained from Pharmacia (Uppsala, Sweden).

The chemicals used in protocol R have been described herein.

Reverse transcriptase SuperScript II was purchased from Life Technologies (Gaithersburg, Md., USA). DNA polymerase Sequenase 2 was obtained from Amersham (United Kingdom). Ampli-Taq DNA polymerase was obtained from Perkin Elmer (Norwalk, USA). RNAse H was obtained from Boehringer (Mannheim, Germany). Salmon sperm DNA was obtained from Sigma (St. Louis, USA).

Composition of Buffers and Solutions.

The preparation of the buffers used in protocol R have been described herein, except that the lysis buffer and washing buffers (L10, L11, and L2) used in protocol R for the isolation of nucleic acids were filtered through a column packed with Diatoms (11) in order to remove any endogenous nucleic acids in the lysis buffer and washing buffers.

The 10× reverse transcription buffer (CMB1) consists of 100 mM Tris.HCl (pH 8.5), 500 mM KCl and 1% TRITON X-100™ (polyethoxylated p-isooctyl-phenol).

The 10×PCR buffer consists of 500 mM Tris.HCl (pH 8.3), 200 mM KCl and 1 mg/ml BSA.

The elution buffer Tris/EDTA (TE, pH 8.0) consists of 10 mM Tris.HCl (pH 8.0) and 1 mM EDTA (pH 8.0).

Oligonucleotides.

The first strand primer TAG 20:

5'GACAGAATGCCGAAATGACCCCNNNNNG3' (SEQ ID NO:1)

The second strand primer TAG 7:

5'DIG-GACAGAATGCCGAAATGANNNNNG3' (SEQ ID NO:2)

The POR primer RB 8:

5'GACAGAATGCCGAAATGA3' (SEQ ID NO:3)

underlined: PCR motif bold: motif for direct sequencing

N=A, T, C, or G

Protocol for First Strand Synthesis.

ss-RNA, present in the commercially available reverse transcriptases, appeared to produce unwanted side products when used in first strand synthesis. To overcome this problem reverse transcriptase was first pretreated in a mixture for cDNA synthesis lacking exogenously added primers:

| 1 μl SuperScript II | (200 U/μl) |
| 1 μl CMB1 | (10×) |
| 0.5 μL MgCl$_2$ | (100 mM) |
| 0.4 μL dNTP's | (25 μM each) |
| 7.1 μL H$_2$O | |
| Incubate 15 min. at 37° C. | |

Nucleic acids (20 μl) purified by protocol R-sup were incubated for 5 min. at 60° C. and thereafter quenched on ice. Subsequently the following mixture was added:

| 3 μl CMB1 | (10×) |
| 1 μl TAG 20 | (100 ng/μl) |
| 1.5 μL MgCl$_2$ | (100 mM) |
| 1.2 μl dNTP's | (25 mM each) |
| 3.3 μl H$_2$O | |

Finally 10 μl of the preincubated Superscript II (SS II) was added and the resulting mixture was incubated for 30 min. at 42° C.

After the reverse transcription reaction SS II was inactivated by incubating the mixture for 5 min. at 80° C., and the mixture was subsequently cooled down to room temperature. In order to convert the RNA/DNA hybrids into single-stranded cDNA twenty units of RNAse H were added to the mixture and incubated for 60 min. at 37° C. The single-stranded cDNA was subsequently isolated using protocol R-sup. The single-stranded cDNA was eluted in 40 μl TE and 20 μl was used as input for second strand synthesis.

Protocol for Second Strand Synthesis.

To twenty microliters of single-stranded cDNA, the following mixture was added (on ice):

| 4 μl CMB1 | (10×) |
| 1 μl TAG 7-DIG* | (100 ng/μl) |
| 2 μl MgCl$_2$ | (100 mM) |
| 1.6 μl dNTP's | (25 mM each) |
| 0.2 μl Sequenase 2 | (13 U/μl) |
| 11.2 μl H$_2$O | |

The mixture was incubated for 10 min. on ice, and subsequently for 60 min. at 37° C. After the second strand synthesis the double-stranded cDNA was isolated using protocol R-pellet. The double-stranded cDNA was eluted in 40 μl TE. Twenty microliters was taken off and 2 μl was used as input for PCR. The remaining 18 μl was stored at −20° C.

Protocol for the Polymerase Chain Reaction.

Two microliters of double-stranded cDNA was added to 48 μl of a PCR mixture consisting of:

| 18 μl TE | (pH 8.0) |
| 1 μl RB 8 | (100 ng/μl) |
| 5 μl PCR buffer | (10×) |
| 0.9 μl MgCl$_2$ | (100 mM) |
| 0.2 μl dNTP's | (100 μM) |
| 0.1 μl dUTP* | (25 μM) |
| 0.3 μl Ampli Taq | (5 U/μl) |
| 22.5 μl H$_2$O | |

After incubation for 5 min. at 95° C. the sample was subjected to 45 cycles of amplification in a DNA thermal cycler (type 480; Perkin Elmer Cetus). A cycle consisted of denaturation for 1 min. at 95° C., annealing for 1 min. at 63° C., and elongation for 2 min. at 72° C. After cycling the sample was incubated for 8 min. at 72° C., and subsequently the temperature was lowered to 4° C. Twenty-five microliter of the PCR product was examined by agarose gel electrophoresis and ethidium bromide staining. In every experiment TE was used as a negative extraction control and as a negative PCR control.

Partial substitution of dTTP with dUTP provides a methodology for ensuring that products from previous PCR reactions cannot be reamplified. Products of PRC amplifications will be uracil-containing deoxyribonucleic acids. Possible contaminating PCR products from a previous PCR amplification will be eliminated by excising uracil bases using the enzymes Uracil N-glycosylase (UNG) prior to PCR (25)

Gel Electrophoresis.

In all experiments, the nucleic acids were electrophoresed (8 to 10 V/cm) through neutral agarose slab gels containing ethidium bromide (1 μg/ml) in the buffer system as described by Aaij and Borst (14)

Hybridization.

DNA fragments were detected after Southern blotting (15) by hybridization with $^{32}$P-labelled probes representing the entire GAG, POL, and ENV genes of HIV-1 [plasmid 5' NOT Hxb$_2$ENN and plasmid 168 1 RTN] (10).

Results

Figure 8:
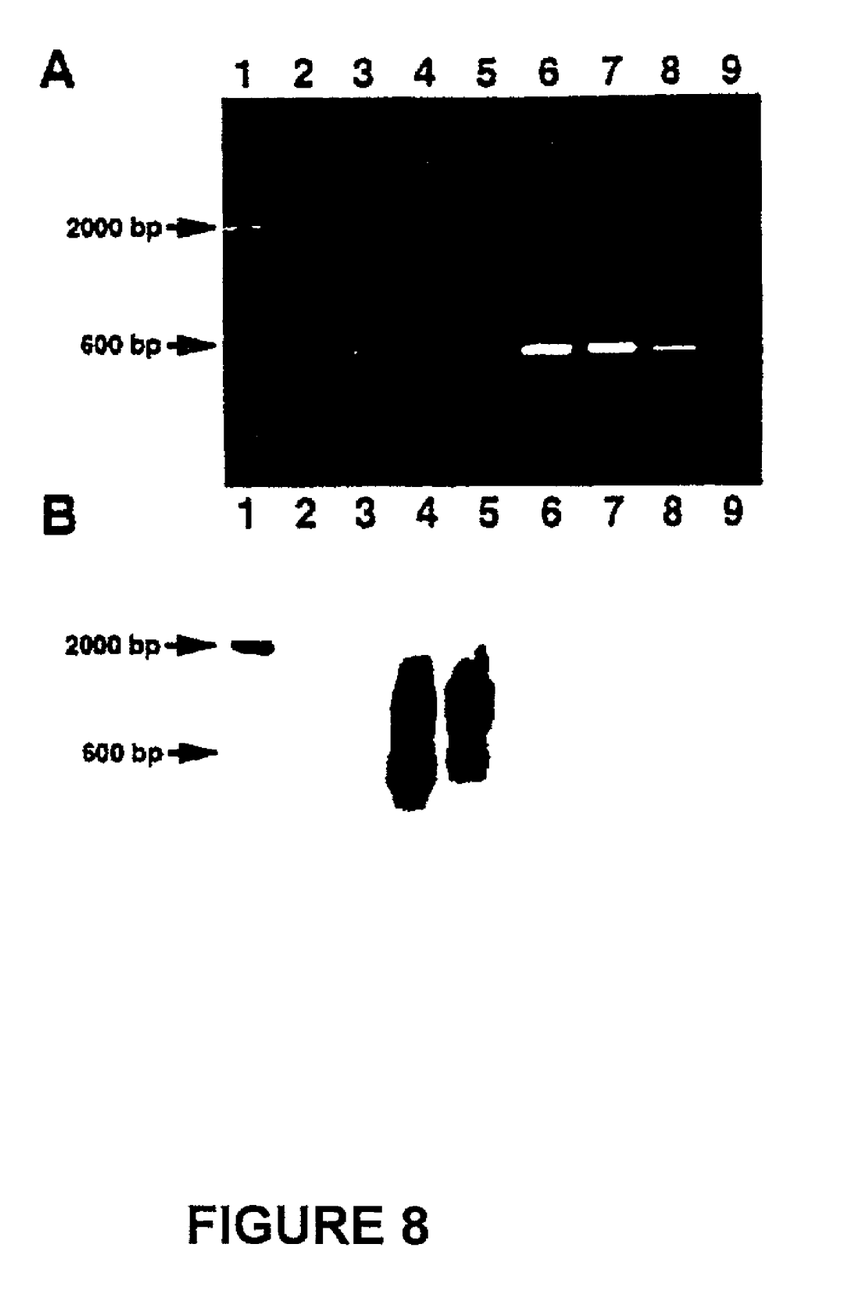

In parallel, $10^5$ molecules of HIV-1 RNA (23) and negative controls (TE) were extracted using protocol R-sup. The resulting single-stranded nucleic acids were amplified by the non-selective RT-PCR as disclosed above, resulting in a discrete banding pattern for HIV-1 RNA, and no amplification products in the TE controls (FIG. 8). The variation between the duplicates is a reflection of the non-selectivity of the procedure. As a control for the efficiency of the PCR part of the procedure we used an input of 0, 6, 60 and 600 molecules of the plasmid pHCrec.

In order to confirm the HIV origin of the bands visible in FIG. 8A, we performed a Southern blot hybridization under high stringency conditions with $^{32}$P-labelled probes encompassing almost the entire HIV-1 genome (FIG. 8B). This experiment showed that most of the bands visible by UV-illumination hybridized with the HIV-1 probe. The bands that did not hybridize with the probe might be homologous to parts of the HIV-1 genome other than those present in the probe or might originate from single-stranded RNA present in the HIV-1 RNA preparation (e.g. cellular mRNA) or ss-RNA present in Superscript II, which was not converted to ds-hybrids during the preincubation of the SuperScript II.

Similar results were obtained with other single-stranded RNAs such as hepatitis C virus RNA, phage MS2 RNA, and the 7.5 Kb Poly(A)-Tailed RNA (results not shown).

It is concluded that the described procedure can be used to amplify single stranded RNA targets (present in e.g. serum) to a series of discrete bands in agarose gels. The discrete bands can be purified from agarose gels, cloned in e.g. a bacterial vector and the clones can subsequently be sequenced. Due to the fact that one of the tagging primers (TAG 20) harbours a sequence motif it is possible to sequence the discrete bands without cloning, after the bands are purified from gel. The method described here is useful in isolating and characterizing unknown sequences present in clinical samples (e.g. viral sequences) or for the amplification of cDNAs from transcripts without having any sequence data.

REFERENCES

1. Serwer, P.(1989) *Electrophoresis*, 10 (5–6), 327–331.
2. Shain, D. H., Yoo, J., Slaughter, R. G., Hayes, S. E. and Tae H. J. (1992) *Anal. Biochem.*, 200, 47–51.
3. Sheer, D. G., Yamane, D. K., Hawke, D. H. and Yuan, P. (1990) *Biotechniques*, 9, 486–495.
4. Mirkes, P. E. (1985) *Anal. Biochem.*, 148 (2), 376–383.
5. Holstege, C. P., Pickaart, M. J. and Louters, L. L. (1988) *J. Chromatogr.*, 455, 401–405.
6. Thompson, J. A. (1986) *Biochromatograpbry*, 1, 68–80.
7. Stowers, D. J., Keim, J. M., Paul, P. S., Lyoo, Y. S., Merion, M. and Benbow, R. M. (1988) *J. Chromatogr.*, 444, 47–65.
8. Liautard, J. P. (1992) *J. Chromatogr.*, 584, 135–139.
9. Chomczynski, P. and Sacchi, N. (1989) *Anal. Biochemn.*, 162, 156–159.
10. Siebert, P. D. and Chenchik, A. (1993) *Nuclcleic Acids Res.*, 21, 2019–2020.
11. Boom, R., Sol, C. J. A., Salimans, M. M. M., Wertheim van Dillen, P. M. E. and van der Noordaa, J. (1990) *J. Clin. Microbiol.*, 28, 495–503.
12. Boom, R., Sol, C. J. A., Heijtink, R., Wertheim van Dillen, P. M. E. and van der Noordaa, J. (1991) *J. Clin. Microbiol.*, 29, 1804–1811.
13. Ish-Horowicz, D. and Burke, J. F. (1981) *Nucleic. Acids Res.*, 9, 2989–2998.
14. Aaij, C., and Borst, P. (1972) *Biochim. Biophys. Acta.*, 269, 192–200.
15. Southern, E. M. (1975) *J. Mol. Biol.*, 98, 503–517.

TABLE 1

| NA-type | binding in L6 | binding in L11 |
|---|---|---|
| ds-DNA | + | + |
| ds-RNA | + | + |
| ss-DNA | + | − |
| ss-RNA | + | − |

Binding of different NA-types to silica particles in different lysisbuffers: similar results were obtained using diatoms rather than silica particles (data not shown).

We claim:

1. A method for separating single stranded nucleic acid from double stranded nucleic acid, comprising the steps of:
   contacting a mixture comprising both single stranded nucleic acid and double stranded nucleic acid with a first liquid comprising a chaotropic agent and a nucleic acid binding solid phase, wherein the first liquid has a composition such that the double stranded nucleic acid binds to the solid phase;
   separating the solid phase from a supernatant containing the single stranded nucleic acid; and
   contacting the supernatant with a second nucleic acid binding solid phase, and a second liquid consisting essentially of material selected from the group consisting of:
   a) a chaotropic agent
   b) a chaotropic agent and a chelating agent;
   c) a chaotropic agent and divalent positive ions; and
   d) a chaotropic agent, a chelating agent and divalent positive ions,
   wherein the second liquid has a composition such that the resulting mixture of supernatant and second liquid allows for binding of the single stranded nucleic acid to the second solid phase.

2. The method according to claim 1, wherein the first liquid comprises a chaotropic agent in concentration between about 1–10M, and a chelating agent, and has a pH between about 2 and 10.

3. The method according to claim 2, wherein the chelating agent is EDTA, which is present in a concentration between about 10 mM and 1M.

4. The method according to claim 3, wherein the first liquid comprises at least about 100 mM EDTA and guanidinium salt as a chaotropic agent.

5. The method according to claim 1, wherein the chaotropic agent is guanidinium thiocyante.

6. The method according to claim 5, whereby the first liquid has the constitution of a buffer prepared by dissolving about 120 g guanidinium thiocyanate in about 1 ml 0.2M EDTA (pH=8).

7. The method according to claim 1, wherein the solid phase is silicum based.

8. The method according to claim 7, wherein the solid phase is silica.

9. The method according to claim 8, wherein the silica is in the form of particles having a size between about 0.05 and about 500 micrometers.

10. The method according to claim 1, wherein the solid phase is separated from the supernatant by centrifugation.

11. The method according to claim 1, wherein the concentration of the divalent positive ions is the same as the concentration of the chelating agent.

12. The method according to claim 1, wherein the chelating agent is EDTA and the ions are $Mg^{2+}$ ions.

13. The method according to claim 1, wherein the chaotropic agent is a guanidinium salt.

14. The method according to claim 1, wherein the second liquid has the constitution of a buffer prepared by dissolving about 120 g guanidinium isothiocyanate in about 100 ml 0.35M TRIS HCl (pH 6.4) and adding about 22 ml 0.2 M EDTA (pH 8.0) and about 9.1 g Triton X-100™ (polyethoxylated p-isooctyl-phenol), homogenizing the solution and adding $MgCl_2$ to a final concentration of about 0.25M.

* * * * *

UNITED STATES PATENT AND TRADEMARK OFFICE
CERTIFICATE OF CORRECTION

PATENT NO. : 7,238,530 B2  
APPLICATION NO. : 09/760085  
DATED : July 3, 2007  
INVENTOR(S) : Goudsmit et al.

It is certified that error appears in the above-identified patent and that said Letters Patent is hereby corrected as shown below:

On Title Page:

Sec (30): Should read --Feb. 14, 1996 (EP) ….. 96200354.7--

Sec (57) Abstract: Line 6 should read --conditions such as--
Line 16 should read --For very efficient separations,--

Column 1, Line 27: Please correct "blood with"
To read --blood, with--

Column 2, Line 1: Please correct "therefore provides"
To read --therefore, provides--

Column 3, Line 4: Please correct "E. coil"
To read --E. coli--

Column 8, Line 11: Please correct "Again are the recoveries"
To read --Again the recoveries--

Column 9, Line 4: Please correct "from Boehninger"
To read --from Boehringer--

Column 9, Line 46: Please correct "The POR primer RB 8:"
To read --The PCR primer RB 8:--

UNITED STATES PATENT AND TRADEMARK OFFICE
CERTIFICATE OF CORRECTION

PATENT NO. : 7,238,530 B2
APPLICATION NO. : 09/760085
DATED : July 3, 2007
INVENTOR(S) : Goudsmit et al.

It is certified that error appears in the above-identified patent and that said Letters Patent is hereby corrected as shown below:

Column 12, Line 23: Please add missing references 16 - 27
16. Froussard, P. (1992) Nucleic Acids Res., 20, 2900.
17. Fritz, J.D., Greaser, M.L. and Wolff, J.A. (1991) Nucleic Acids Res., 19, 3747.
18. Frohman, M.A., Dush, M.K. and Martin, G.R. (1988) Proc. Natl. Acad. Sci., 85, 8998-9002.
19. Schlayer, H. –J., Peters, T., Preisler, S., Fehr, J., Gerok, W. and Rasenack, J. (1992) J. Virol. Methods, 38, 333-341.
20. Trout, A.B., McHeyzer-Williams, M.G., Pulendran, B. and Nossal, J.V. (1992) Proc. Natl. Acad. Sci., 89, 9823-9825.
21. Akowitz, A. and Manuelidis, L. (1989) Gene, 81, 295-306.
22. Fukuoka, S. –I. and Scheele, G.A. (1991) Nucleic Acids Res., 19, 6961.
23. Layne, S.P., Merges, M.J., Dembo, M., Spouge, J.L., Conley, S.R., Moore, J.P., Raina, J.L., Renz, H., Gelderblom, H.R. and Nara, P.L. (1992) Virology, 189, 695-714.
24. de Jong, J., Goudsmit, J., Keulen, W., Klaver, B., Krone, W., Tersmette, M. and de Ronde, T. (1992) J. of Virol., 66, 757-765.
25. Varshney, U., et al. (1988) J. Biol. Chem., 263, 7776-7784.
26. Van Ness et al. Nucleic Acids Research, vol. 9, No. 19, pp. 5143-5151.
27. Thompson et al. Anal. Biochem., vol 3, pp. 281-291, 1987.

Signed and Sealed this

Eighth Day of January, 2008

JON W. DUDAS
*Director of the United States Patent and Trademark Office*